(12) United States Patent
Varieur et al.

(10) Patent No.: US 7,824,413 B2
(45) Date of Patent: *Nov. 2, 2010

(54) INSTRUMENTS AND METHODS FOR BONE ANCHOR ENGAGEMENT AND SPINAL ROD REDUCTION

(75) Inventors: Michael S Varieur, Portsmouth, RI (US); Thomas J Runco, Canton, MA (US)

(73) Assignee: Depuy Spine, Inc., Raynham, MA (US)

( * ) Notice: Subject to any disclaimer, the term of this patent is extended or adjusted under 35 U.S.C. 154(b) by 983 days.

This patent is subject to a terminal disclaimer.

(21) Appl. No.: 11/013,180

(22) Filed: Dec. 15, 2004

(65) Prior Publication Data

US 2005/0149053 A1 Jul. 7, 2005

Related U.S. Application Data (60) Provisional application No. 60/530,179, filed on Dec. 17, 2003.

(51) Int. Cl.
A61B 17/58 (2006.01)
A61B 17/60 (2006.01)
A61F 2/00 (2006.01)

(52) U.S. Cl. .................. 606/99; 606/104; 606/279

(58) Field of Classification Search .......... 606/86, 606/99, 103, 104; 81/3.8, 44, 53.1, 53.11, 81/53.12

See application file for complete search history.

(56) References Cited

U.S. PATENT DOCUMENTS

| | | | |
|---|---|---|---|
| 410,780 A | 9/1889 | Cahn |
| 445,513 A | 1/1891 | Powell |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes |
| 1,925,385 A | 9/1933 | Humes |

(Continued)

FOREIGN PATENT DOCUMENTS

DE 4238339 A1 5/1994

(Continued)

OTHER PUBLICATIONS

Office action mailed on Jan. 11, 2008 for U.S. Appl. No. 11/013,258.

(Continued)

*Primary Examiner*—Thomas C Barrett
*Assistant Examiner*—Andrew Yang (57) ABSTRACT

An instrument for engaging a bone anchor may include a first implant engaging member having a proximal end and a distal end and a second implant engaging member having a proximal end and a distal end. The second implant engaging member may be pivotally connected to the first implant engaging member about a pivot point located proximate the distal ends of the first and second implant engaging members. Manipulation of the proximal ends of the first and second implant engaging member can cause each of the distal ends to rotate about the pivot point to engage at least a portion of a bone anchor. A rod adjusting tool may be connectable to the bone anchor engaging tool and may be axially adjustable relative to the bone anchor tool to adjust a spinal rod relative to the bone anchor.

18 Claims, 12 Drawing Sheets

U.S. PATENT DOCUMENTS

| | | | |
|---|---|---|---|
| 2,248,054 A | 7/1941 | Becker | |
| 2,248,057 A | 7/1941 | Bond | |
| 2,291,413 A | 7/1942 | Siebrandt | |
| 2,370,407 A | 2/1945 | Ray McCartney | |
| 2,800,820 A | 7/1957 | Retterath | |
| 3,960,147 A * | 6/1976 | Murray | 606/75 |
| 4,237,875 A | 12/1980 | Termanini | |
| 4,271,836 A | 6/1981 | Bacala | |
| 4,411,259 A | 10/1983 | Drummond | |
| 4,445,513 A | 5/1984 | Ulrich | |
| 4,655,223 A | 4/1987 | Kim | |
| 4,809,695 A | 3/1989 | Gwathmey | |
| 4,896,661 A | 1/1990 | Bogert | |
| 5,014,407 A | 5/1991 | Boughten | |
| 5,020,519 A | 6/1991 | Hayes et al. | |
| 5,364,397 A | 11/1994 | Hayes | |
| 5,391,170 A | 2/1995 | McGuire | |
| 5,429,641 A | 7/1995 | Gotfried | |
| 5,484,440 A | 1/1996 | Allard | |
| 5,545,165 A | 8/1996 | Biedermann | |
| 5,551,320 A | 9/1996 | Horobec | |
| 5,616,143 A | 4/1997 | Schlapfer | |
| 5,649,931 A | 7/1997 | Bryant | |
| 5,697,933 A | 12/1997 | Gundlapalli | |
| 5,707,371 A | 1/1998 | Metz-Stavenhagen | |
| 5,720,751 A | 2/1998 | Jackson | |
| 5,725,532 A | 3/1998 | Shoemaker | |
| 5,746,757 A | 5/1998 | McGuire | |
| 5,782,831 A | 7/1998 | Sherman | |
| 5,810,878 A | 9/1998 | Burel | |
| 5,910,141 A | 6/1999 | Morrison et al. | |
| 5,951,564 A * | 9/1999 | Schroder et al. | 606/100 |
| 5,951,579 A | 9/1999 | Dykes | |
| 6,010,509 A | 1/2000 | Delgado | |
| 6,036,692 A | 3/2000 | Burel | |
| 6,099,528 A | 8/2000 | Saurat | |
| 6,123,707 A | 9/2000 | Wagner | |
| 6,139,549 A | 10/2000 | Keller | |
| 6,183,472 B1 | 2/2001 | Lutz | |
| 6,210,330 B1 | 4/2001 | Tepper | |
| 6,251,112 B1 | 6/2001 | Jackson | |
| 6,258,090 B1 | 7/2001 | Jackson | |
| 6,371,973 B1 | 4/2002 | Tepper | |
| 6,440,133 B1 | 8/2002 | Beale et al. | |
| 6,440,142 B1 | 8/2002 | Ralph | |
| 6,511,484 B2 | 1/2003 | Torode | |
| 6,530,929 B1 | 3/2003 | Justis | |
| 6,589,249 B2 | 7/2003 | Sater | |
| 6,648,888 B1 | 11/2003 | Shluzas | |
| 6,660,006 B2 | 12/2003 | Markworth | |
| 6,726,692 B2 | 4/2004 | Bette | |
| 6,743,231 B1 | 6/2004 | Gray | |
| 6,746,449 B2 | 6/2004 | Jones | |
| 6,752,832 B2 | 6/2004 | Neumann | |
| 6,755,829 B1 | 6/2004 | Bono | |
| 6,790,208 B2 | 9/2004 | Oribe | |
| 6,790,209 B2 | 9/2004 | Beale | |
| 6,827,722 B1 | 12/2004 | Schoenfeld | |
| 7,083,621 B2 | 8/2006 | Shaolian | |
| 7,156,849 B2 | 1/2007 | Dunbar | |
| 7,179,254 B2 | 2/2007 | Pendekanti | |
| 7,179,261 B2 | 2/2007 | Sicvol | |
| 7,278,995 B2 | 10/2007 | Nichols | |
| 7,462,182 B2 | 12/2008 | Lim | |
| 7,491,207 B2 | 2/2009 | Keyer | |
| 7,527,638 B2 | 5/2009 | Anderson | |
| 7,572,281 B2 | 8/2009 | Runco | |
| 7,666,188 B2 | 2/2010 | Anderson | |
| 7,708,763 B2 | 5/2010 | Selover | |
| 2001/0029376 A1 | 10/2001 | Sater | |
| 2002/0095153 A1 | 7/2002 | Jones | |
| 2003/0028195 A1 | 2/2003 | Bette | |
| 2003/0125750 A1 | 7/2003 | Zwirnmann | |
| 2003/0149438 A1 | 8/2003 | Nichols | |
| 2003/0191370 A1 | 10/2003 | Phillips | |
| 2003/0199872 A1 | 10/2003 | Markworth | |
| 2004/0036254 A1 | 2/2004 | Patton | |
| 2004/0049191 A1 | 3/2004 | Markworth | |
| 2004/0147936 A1 | 7/2004 | Rosenberg | |
| 2004/0147937 A1 | 7/2004 | Dunbar | |
| 2004/0172057 A1 | 9/2004 | Guillebon | |
| 2004/0176779 A1 | 9/2004 | Cassutt | |
| 2004/0220567 A1 | 11/2004 | Eisemann | |
| 2004/0254576 A1 | 12/2004 | Dunbar | |
| 2004/0267275 A1 | 12/2004 | Cournoyer | |
| 2005/0015095 A1 * | 1/2005 | Keller | 606/99 |
| 2005/0055031 A1 | 3/2005 | Lim | |
| 2005/0059969 A1 | 3/2005 | McKinley | |
| 2005/0079909 A1 | 4/2005 | Singhaseni | |
| 2005/0090824 A1 | 4/2005 | Shluzas | |
| 2005/0131408 A1 | 6/2005 | Sicvol | |
| 2005/0131420 A1 | 6/2005 | Techiera | |
| 2005/0131422 A1 | 6/2005 | Anderson | |
| 2005/0143749 A1 | 6/2005 | Zalenski | |
| 2005/0149036 A1 | 7/2005 | Varieur | |
| 2005/0149048 A1 | 7/2005 | Leport | |
| 2005/0149053 A1 | 7/2005 | Varieur | |
| 2005/0192570 A1 | 9/2005 | Jackson | |
| 2005/0192579 A1 | 9/2005 | Jackson | |
| 2005/0228392 A1 | 10/2005 | Keyer | |
| 2005/0261702 A1 | 11/2005 | Oribe | |
| 2006/0009775 A1 | 1/2006 | Dec | |
| 2006/0025768 A1 | 2/2006 | Iott | |
| 2006/0036254 A1 | 2/2006 | Lim | |
| 2006/0036260 A1 | 2/2006 | Runco | |
| 2006/0074418 A1 | 4/2006 | Jackson | |
| 2006/0079909 A1 | 4/2006 | Runco | |
| 2006/0089651 A1 | 4/2006 | Trudeau | |
| 2006/0095035 A1 | 5/2006 | Jones | |
| 2006/0111730 A1 | 5/2006 | Hay | |
| 2006/0166534 A1 | 7/2006 | Brumfield | |
| 2006/0166535 A1 | 7/2006 | Brumfield | |
| 2006/0293692 A1 | 12/2006 | Whipple | |
| 2007/0093849 A1 | 4/2007 | Jones | |
| 2007/0129731 A1 | 6/2007 | Sicvol | |
| 2007/0161998 A1 | 7/2007 | Whipple | |
| 2007/0167954 A1 | 7/2007 | Sicvol | |
| 2007/0173831 A1 | 7/2007 | Abdou | |
| 2007/0213722 A1 | 9/2007 | Jones | |
| 2007/0233097 A1 | 10/2007 | Anderson | |
| 2007/0260261 A1 | 11/2007 | Runco | |
| 2008/0077134 A1 | 3/2008 | Dziedzic | |
| 2008/0077135 A1 | 3/2008 | Stad | |
| 2008/0243190 A1 | 10/2008 | Dziedzic | |
| 2008/0255574 A1 | 10/2008 | Dye | |
| 2009/0030419 A1 | 1/2009 | Runco | |
| 2009/0054902 A1 | 2/2009 | Mickiewicz | |
| 2009/0082811 A1 | 3/2009 | Stad | |
| 2009/0088764 A1 | 4/2009 | Stad | |
| 2009/0138056 A1 | 5/2009 | Anderson | |
| 2009/0143828 A1 | 6/2009 | Stad | |
| 2010/0137915 A1 | 6/2010 | Anderson | |

FOREIGN PATENT DOCUMENTS

| | | |
|---|---|---|
| EP | 1648320 | 1/2005 |
| EP | 1574175 | 9/2005 |
| EP | 1796564 | 2/2006 |
| FR | 2677242 | 5/1991 |
| FR | 2729291 | 7/1996 |

| | | |
|---|---|---|
| WO | 9621396 | 7/1996 |

OTHER PUBLICATIONS

Response to office action filed by applicant on May 8, 2008 for U.S. Appl. No. 11/013,258.
Pending U.S. Appl. No. 11/828,684, filed Jul. 26, 2007.
Pending U.S. Appl. No. 11/828,652, filed Jul. 26, 2007.
Office Action mailed on Dec. 23, 2008 for U.S. Appl. No. 11/235,694.
Response filed by applicant on Mar. 23, 2009 for U.S. Appl. No. 11/235,694.
Final Office Action filed by applicant on Jun. 18, 2009 for U.S. Appl. No. 11/235,694.
Response filed by applicant on Sep. 18, 2009 for U.S. Appl. No. 11/235,694.
Response filed by applicant on May 8, 2008 for U.S. Appl. No. 11/013,258.
Office Action mailed on Sep. 3, 2008 for U.S. Appl. No. 11/013,258.
Response filed by applicant on Feb. 2, 2009 for U.S. Appl. No. 11/013,258.
Sofamor "Introducteur—Contreur De Tige", Jun. 1994.

\* cited by examiner

INSTRUMENTS AND METHODS FOR BONE ANCHOR ENGAGEMENT AND SPINAL ROD REDUCTION

REFERENCE TO RELATED APPLICATIONS

This application claims the benefit of U.S. Provisional Application No. 60/530,179 filed on Dec. 17, 2003 which is hereby incorporated by reference.

BACKGROUND

Spinal fixation systems may be used in orthopedic surgery to align and/or fix a desired relationship between adjacent vertebral bodies. Such systems typically include a spinal fixation element, such as a relatively rigid fixation rod or plate, that is coupled to adjacent vertebrae by attaching the element to various anchoring devices, such as hooks, bolts, wires, or screws. The spinal fixation element can have a predetermined contour that has been designed according to the properties of the target implantation site, and once installed, the spinal fixation element holds the vertebrae in a desired spatial relationship, either until desired healing or spinal fusion has taken place, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a spinal fixation element receiving element, which, in spinal rod applications, is usually in the form of a U-shaped slot formed in the head for receiving the rod. A set-screw, plug, cap or similar type of closure mechanism, is used to lock the rod into the rod-receiving portion of the pedicle screw. In use, the shank portion of each screw is then threaded into a vertebra, and once properly positioned, a fixation rod is seated through the rod-receiving portion of each screw and the rod is locked in place by tightening a cap or similar type of closure mechanism to securely interconnect each screw and the fixation rod. Other anchoring devices also include hooks and other types of bone screws.

While current spinal fixation systems have proven effective, difficulties have been encountered in mounting rods into the rod-receiving portion of various fixation devices. In particular, it can be difficult to align and seat the rod into the rod receiving portion of adjacent fixation devices due to the positioning and rigidity of the vertebra into which the fixation device is mounted. Thus, the use of a spinal rod approximator, also referred to as a spinal rod reducer, is often required in order to grasp the head of the fixation device and reduce the rod into the rod-receiving portion of the fixation device.

While several rod approximators are known in the art, some tend to be difficult and very time-consuming to use. Accordingly, there is a need for an improved rod approximator and methods for seating a spinal rod in a rod-receiving portion of one or more spinal implants.

SUMMARY

Disclosed herein are instruments that facilitate the engagement of an instrument, such as a reduction instrument or approximator, to an implant such as a bone anchor. In one exemplary embodiment, an instrument for engaging a bone implant may comprise a first implant engaging member having a proximal end and a distal end and a second implant engaging member having a proximal end and a distal end. The second implant engaging member may be pivotally connected to the first implant engaging member about at least one pivot point located proximate the distal ends of the first and second implant engaging members. In use, manipulation of the proximal ends of the first and second implant engaging members can cause each of the distal ends to rotate about the pivot point to engage at least a portion of an anchor.

In another exemplary embodiment, a rod reduction instrument for adjusting a spinal rod relative to a bone anchor may comprise a bone anchor engaging tool and a rod adjusting tool. The bone anchor engaging tool may include a first jaw member having a proximal end and a distal end and a second jaw member having a proximal end and a distal end. The second jaw member may be pivotally connected to the first jaw member about at least one pivot point located proximate the distal ends of the first and second jaw members. In use, manipulation of the proximal ends of the first and second jaw members can cause each of the distal ends to rotate about the pivot point to engage at least a portion of a bone anchor. The rod adjusting tool, in the exemplary embodiment, may be connectable to the bone anchor engaging tool and may have a proximal end and a distal end. The rod adjusting tool may be axially adjustable relative to the bone anchor tool to adjust a spinal rod relative to the bone anchor.

BRIEF DESCRIPTION OF THE DRAWINGS

These and other features and advantages of the instruments and methods disclosed herein will be more fully understood by reference to the following detailed description in conjunction with the attached drawings in which like reference numerals refer to like elements through the different views. The drawings illustrate principles of the instruments disclosed herein and, although not to scale, show relative dimensions.

DETAILED DESCRIPTION

Certain exemplary embodiments will now be described to provide an overall understanding of the principles of the structure, function, manufacture, and use of the instruments disclosed herein. One or more examples of these embodiments are illustrated in the accompanying drawings. Those of ordinary skill in the art will understand that the instruments specifically described herein and illustrated in the accompanying drawings are non-limiting exemplary embodiments and that the scope of the present invention is defined solely be the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The term "distal" as used herein with respect to any component or structure will generally refer to a position or orientation that is proximate, relatively, to the bone surface to which a bone anchor is to be applied. Conversely, the term "proximal" as used herein with respect to any component or structure will generally refer to a position or orientation that is distant, relatively, to the bone surface to which a bone anchor is to be applied.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Figure 1:
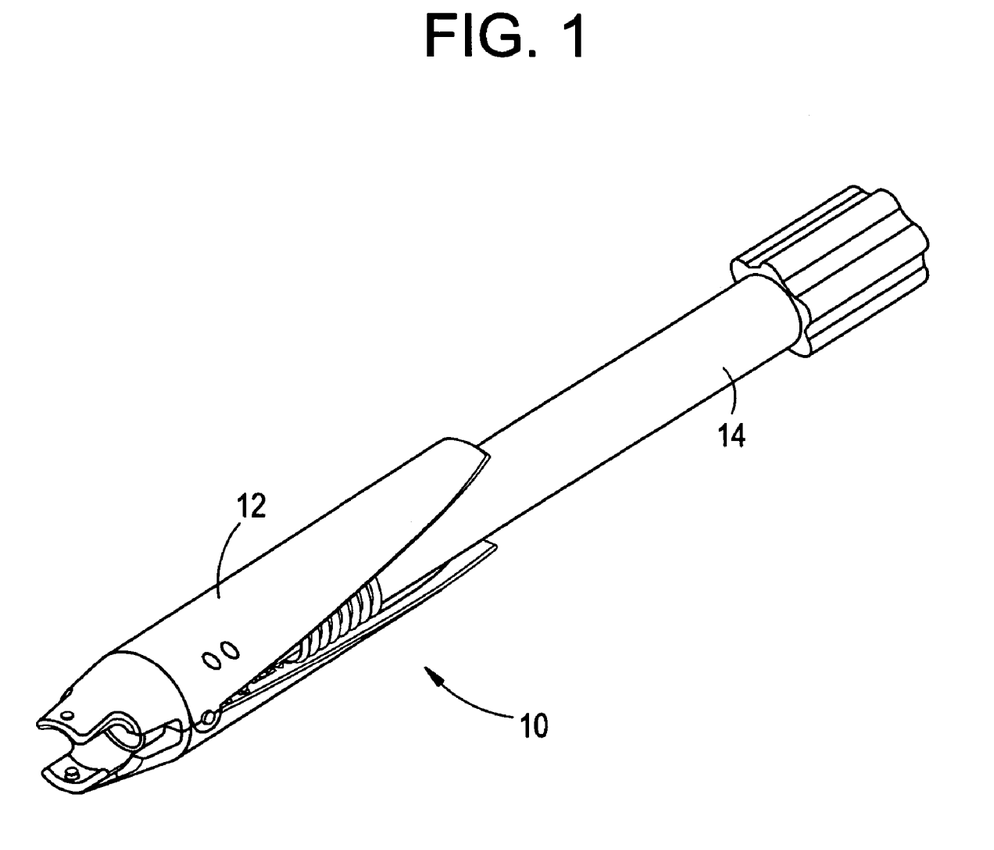
FIG. 1 is a perspective view of an exemplary embodiment of an instrument for adjusting a spinal rod relative to a bone anchor, illustrating a rod adjusting tool positioned within a bone anchor engaging tool.
Figure 2:
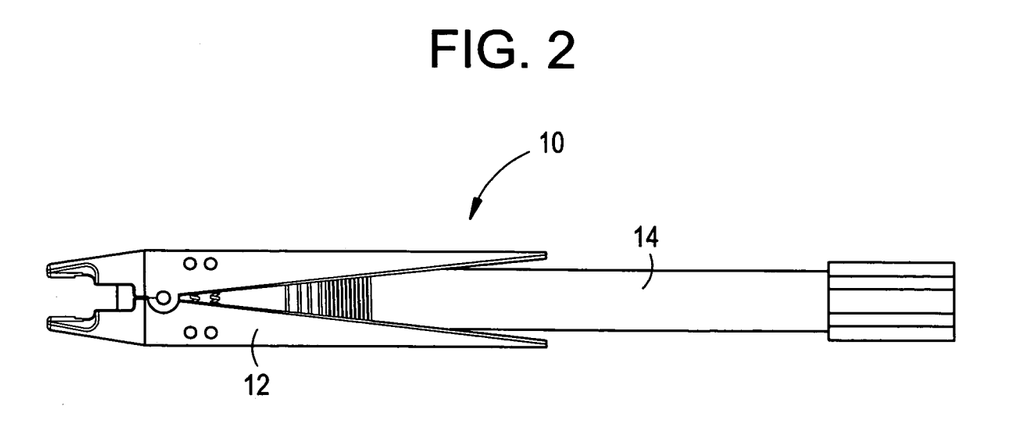
FIG. 2 is a side elevational view of the instrument of FIG. 1.
Figure 3:
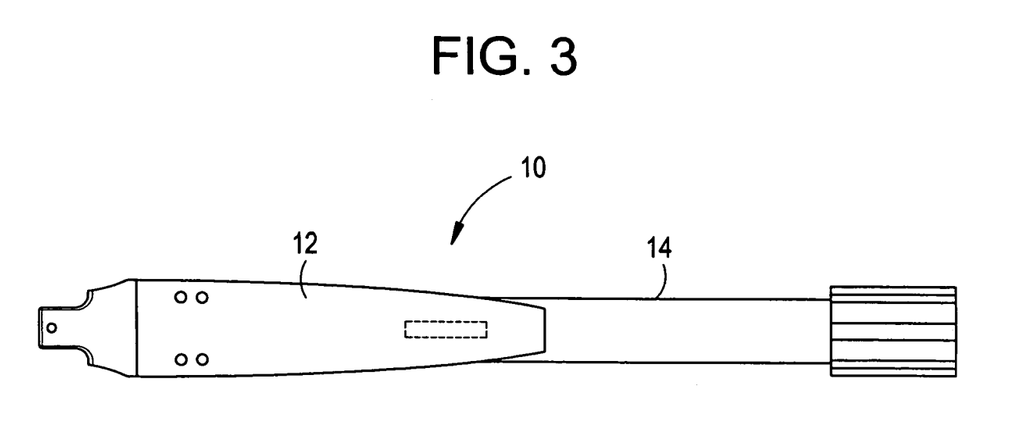
FIG. 3 is a top view of the instrument of FIG. 1.

FIGS. 1-3 illustrate an exemplary embodiment of an instrument 10 for engaging an implant, such as a bone anchor, and positioning a fixation element, such as a spinal rod, relative to the bone anchor. The exemplary instrument 10 may include an implant (e.g., bone anchor) engaging tool 12 for engaging at least a portion of an implant such as a bone anchor. The exemplary bone anchor engaging tool 12 is particular suited for engaging the proximal end of a pedicle screw, although one skilled in the art will appreciate that the exemplary bone anchor engaging tool 12 may be employed with any type of bone anchor. The exemplary instrument 10 may further include a rod adjustment tool 14 that is connectable to the bone anchor engaging tool 12 and may be axially adjustable relative to the bone anchor engaging tool 12. The exemplary rod adjustment tool 14 may be advanced axially to position a spinal rod relative to a bone anchor engaged by the bone anchor engaging tool 12. For example, the rod adjustment tool 14 may be employed to reduce a spinal rod into the rod receiving portion of a pedicle screw that is engaged by the bone anchor engaging tool 12. Although the exemplary instrument 10 is described primarily in connection with spinal applications, one skilled in the art will appreciate that the exemplary instrument 10, as well as the other exemplary embodiments described below, may be used to engage any type of bone anchor or other implant and/or to position any type of fixation element relative to a bone anchor.

Referring to FIGS. 4-9, the exemplary bone engagement tool 10 includes a first jaw member 18A and a second jaw member 18B which can cooperate to engage an implant such as a bone anchor. The first jaw member 18A and the second jaw member 18B, in the exemplary embodiment, are identical in construction and, accordingly, features of the first jaw member 18A discussed below and illustrated in the FIGURES may also be present in the second jaw member 18B. The first jaw member 18A and the second jaw member 18B each have a proximal end 20A,B and a distal end 22A,B space apart approximately a length L, indicated by arrow L in FIG. 5, from the proximal end 20A,B. The jaw members 18A,B have an interior surface 19A,B and an exterior surface 21A,B. The jaw members 18A,B preferably have a length L that is sufficient to span from a skin incision in a patient at the proximal end 20A,B to proximate a vertebra of the patient at the distal end 22A,B thereof. The jaw members 18A,B may be constructed from any biocompatible or sterilizable material, including a metal such as stainless steel, or a polymer.

Figure 4:
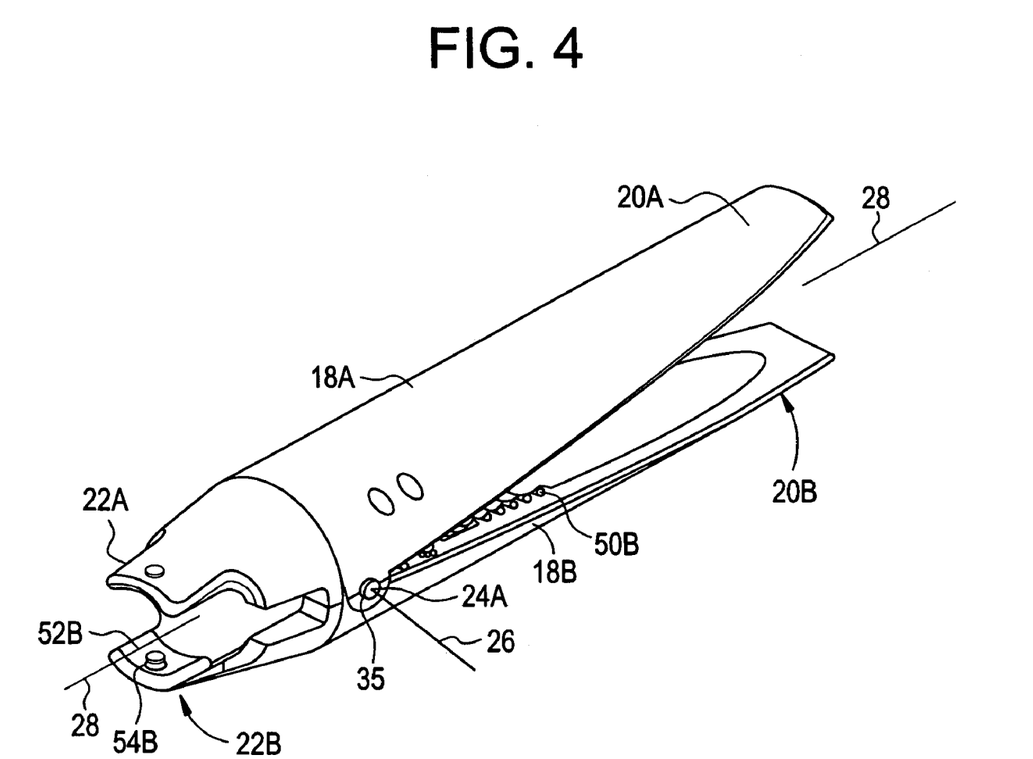
FIG. 4 is a perspective view of the bone anchor engaging tool of FIG. 1.
Figure 5:
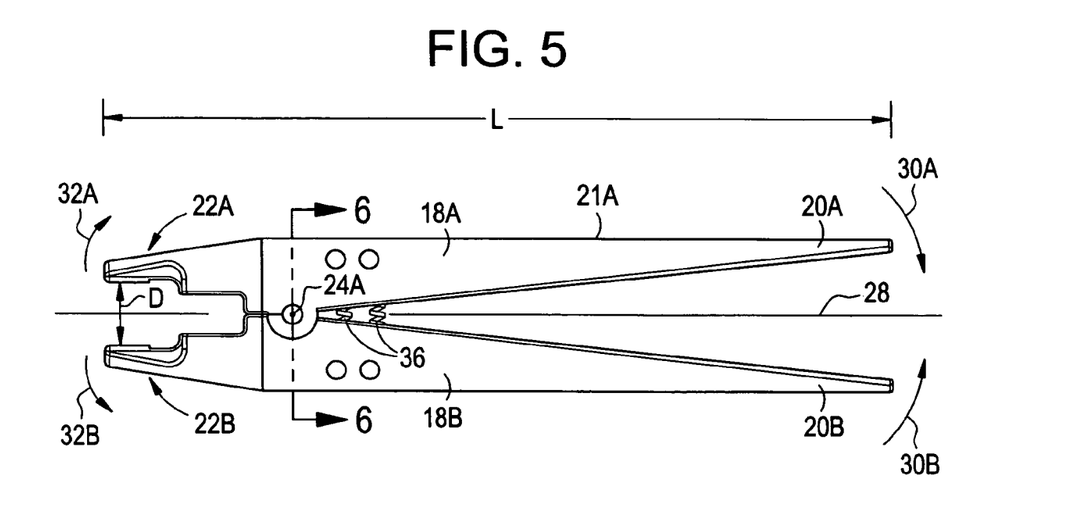
FIG. 5 is a side elevational view of the bone anchor engaging tool of FIG. 4, illustrating the jaw members of the tool in an approximately closed position.
Figure 6:
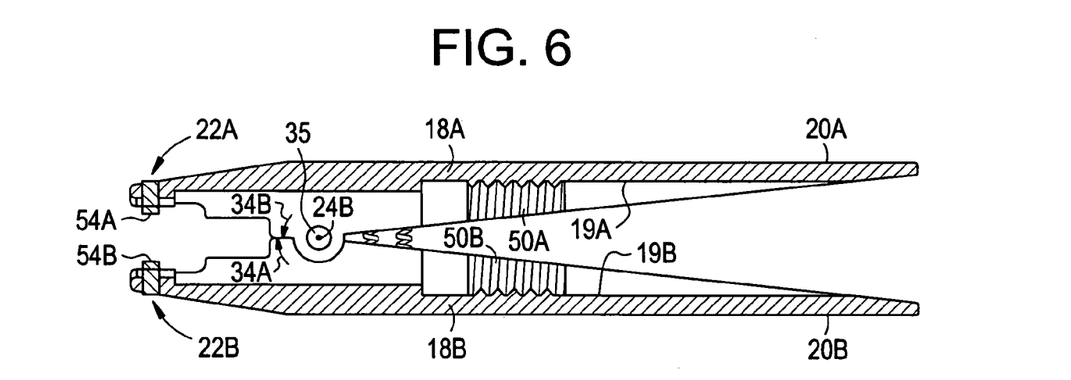
FIG. 6 is a side elevational view in cross-section of the bone anchor engaging tool of FIG. 4, illustrating the jaw members of the tool in an approximately closed position.
Figure 7:
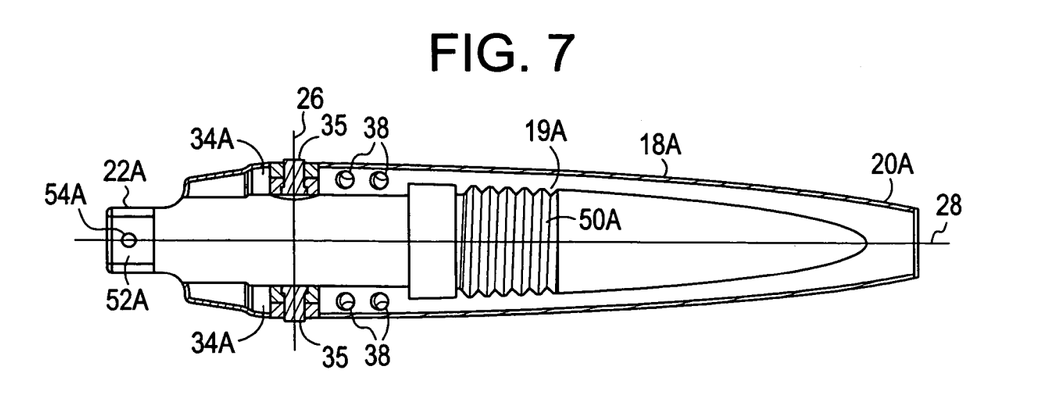
FIG. 7 is a side elevational view of the interior surface of a jaw member of the bone anchor engaging tool of FIG. 4.
Figure 8:
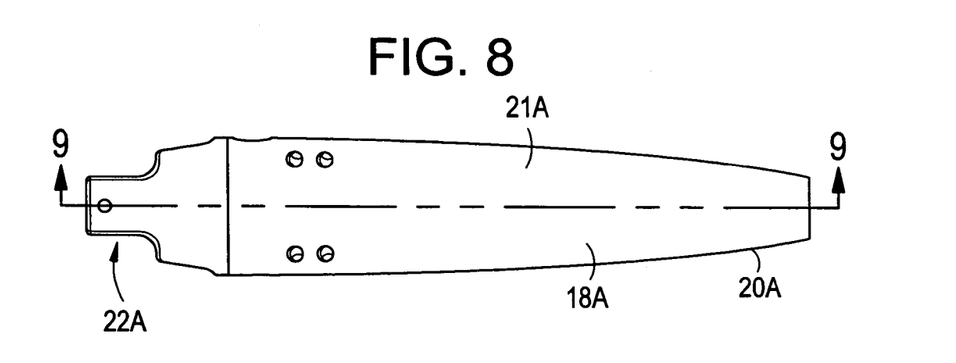
FIG. 8 is a side elevational view of the exterior surface of a jaw member of the bone anchor engaging tool of FIG. 4.
Figure 9:
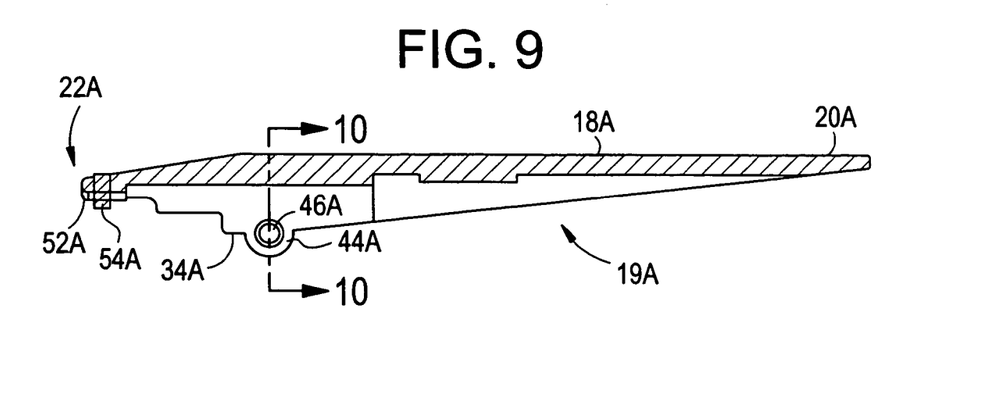
FIG. 9 is a side elevational view in cross-section of the jaw member of FIG. 4, taken along line B-B of FIG. 8.

The first jaw member 18A may be pivotally connected to the second jaw member 18B at a pivot points 24A,B that are aligned along a pivot axis 26. The pivot axis 26, in the illustrated exemplary embodiment, is oriented generally perpendicular to the longitudinal axis 28 of the bone anchor engaging tool 12. The pivot axis 26, in the exemplary embodiment, is positioned proximate the distal ends 22A,B of the jaw members 18A,B, e.g., closer to the distal ends 22A,B of the jaw members 18A,B than the proximal ends 20A,B of the jaw members 18A,B, although the pivot access 26 may be located anywhere along the length of the jaw members. Manipulation of the proximal ends 20A,B of the first jaw member 18A,B causes the distal ends 22A,B to rotate about the pivot points 24A,B. For example, in the exemplary embodiment, compressing the proximal ends 20A,B towards one another, as indicated by arrows 30A,B, causes the distal ends 22A,B to rotate from an approximately closed position in which the jaw members are proximate one another, as indicated by arrows 32A,B, to an open position in which the jaw members are displaced from one another. FIGS. 4-6 illustrate the jaw members 18A,B in the approximately closed position. In the approximately closed position, distal ends 22A,B of the jaw members 18A,B may be separated a distance D that is approximately equal to or less than the extent of the portion of the implant to be engaged by the bone anchor engagement tool 12 to facilitate engagement of an implant when the distal ends 22A,B of the jaw members 18A,B are in the approximately closed position. For example, in the exemplary embodiment, the distance D may be approximately equal to or less than the outer diameter of the rod receiving portion of a pedicle screw. In the exemplary embodiment, axially extending contact surfaces 34A,B define the distance D by limiting the motion of the distal ends 22A,B towards one another. In the open position, the distal ends 22A,B may be displaced a distance greater than distance D to facilitate positioning of the distal ends 22A,B about the implant.

The jaw members 18A,B may be coupled together by one or more pins 35 that may be aligned with and define the pivot axis 26 about which the jaw members 18A,B rotate. The jaw members 18A,B, when pivotally connected, may form an annular collar 40 that is intersected by the pivot axis 26. For example, each jaw member 18A,B may include an arcuate section 42A,42B that may engage to form collar 40. Each arcuate section 42A,B may include a pair of spaced apart tabs 44A,B and 48A,B each having an opening 46 formed therein for receiving a pin 35A,B. When the jaw members 18A,B are engaged, the tabs 44A and 48B engage to form an opening 46A and tabs 44B and 48A engage to form an opening 46B. Each engaged pair of tabs are radially spaced apart from one another and the respective openings 46A,B are aligned to define the pivot axis 26.

The bone engagement tool 12 may include a biasing mechanism coupled to the jaw members 18A,B to bias the distal ends 22A,B to the approximately closed position. The biasing mechanism may be, for example, one or more springs positioned between the jaw members 18A,B. The spring(s) may a coiled spring, a leaf spring, or any other suitable spring. In the exemplary embodiment, two pairs of coiled springs 36 are positioned between the jaw members 18A,B approximate the pivot axis 26. One or more bores 38 may be provided in the jaw members 18A, 18B to seat the springs. The number, location, and structure of the springs may be varied depending on, for example, the amount of biasing force desired.

Figure 10:
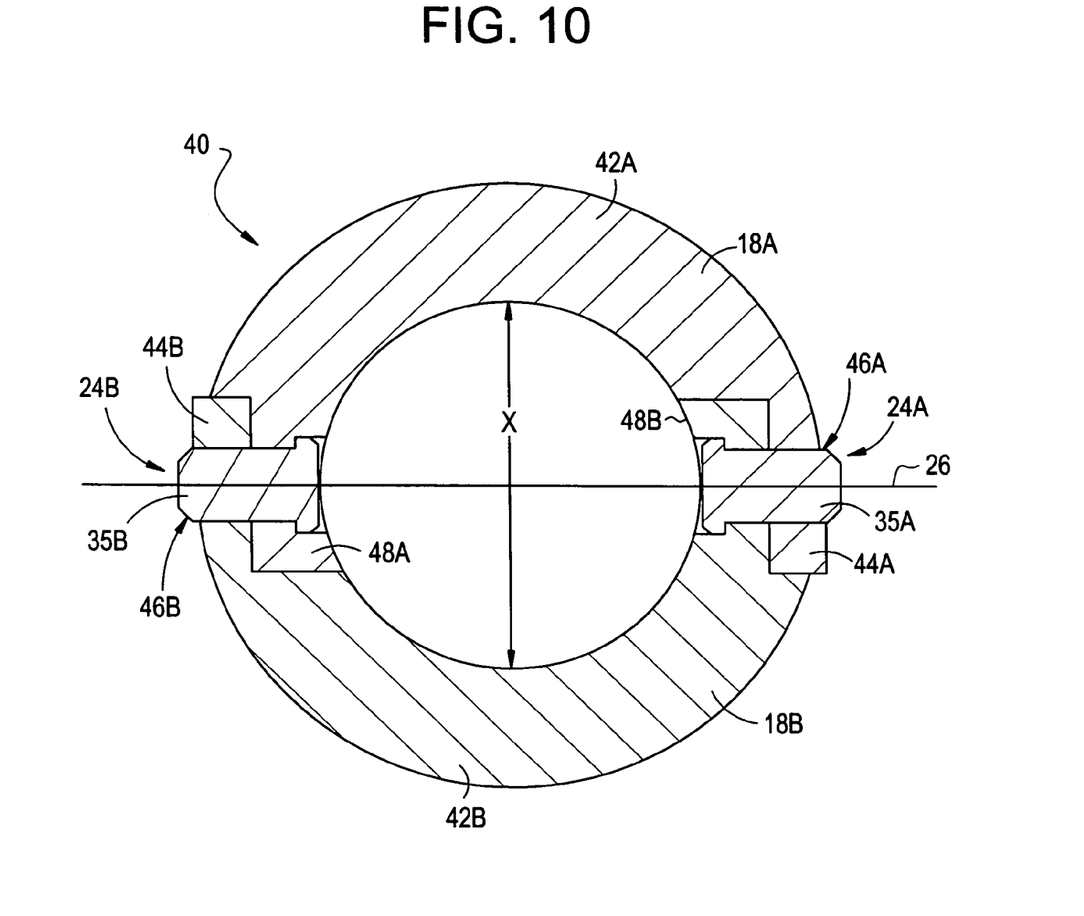
FIG. 10 is a cross sectional view of the collar of the bone anchor engaging tool of FIG. 4, taken along line G-G of FIG. 5.

The jaw members 18A,B may be spaced apart a distance to define an opening therebetween that may be sized and shaped to facilitate the delivery of an implant, such as a component of a bone anchor, or an instrument, such as the rod adjusting tool 14, through the opening. For example, in the illustrated exemplary embodiment, the collar 40 is generally annular in shape and has a diameter, indicated by arrow X in FIG. 10, that is greater than the extent of an implant or instrument to be delivered through the bone anchor engaging tool 12. In the exemplary embodiment, for example the diameter X of the collar may be greater than the diameter of the rod adjusting tool 14 and the closure mechanism of the bone anchor. Likewise, the distance D between the distal ends 22A,B, in the approximately closed position, may be greater than the extent of an implant or instrument to be delivered through the bone anchor engaging tool 12.

The bone anchor engaging tool 12 may include an adjustment mechanism that facilitates the adjustment of a second instrument, such as, for example, the rod adjusting tool 14, along the longitudinal axis 28 of the tool 12. In the illustrated exemplary embodiment, for example, internal threads 50A,B are formed on the interior surface 19A,B for engaging mating external threads formed on the second instrument. The internal threads 50 A,B are preferably ocated proximal to the pivot axis 26. The adjustment mechanism is not limited to threads; one skilled in the art will appreciate that other structures that facilitate axial adjustment of a second instrument may be employed, including, for example, slot(s) or groove(s) formed in the jaw members to receive pin(s) or other structures provided on the second instrument or pin(s) or other projections provided on the interior of the jaw members 18A,B that seat within groove(s) or slot(s) provided on the second instrument.

Although the exemplary embodiment includes an internal adjustment mechanism, e.g., threads 50A,B, one skilled in the art will appreciate that the tool 12 may alternatively include an external adjustment mechanism, in which case the second instrument may be advanced about (e.g., exterior to) the bone anchor engaging tool.

Figure 16A:
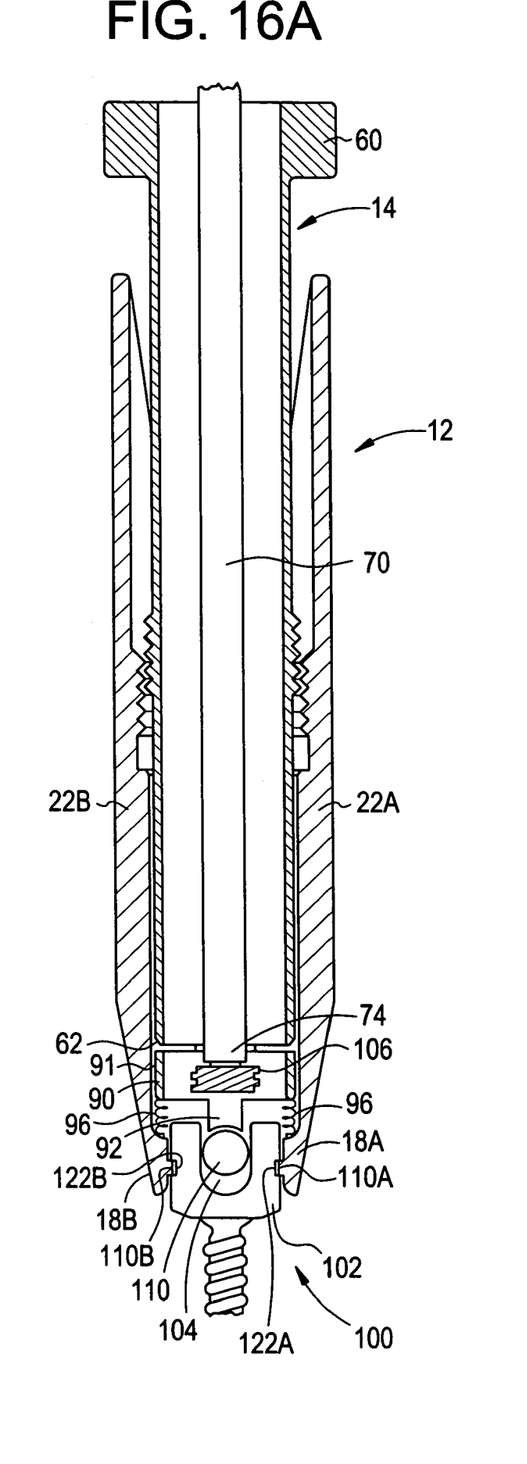
FIG. 16A is a side elevational view in cross-section the distal end of an exemplary embodiment of an instrument for adjusting a spinal rod relative to a bone anchor.

The distal end 22 A,B on one or both of the jaw members 18A,B may include an implant engagement mechanism that provides a releasable connection between the distal end(s) and the implant. For example, the implant engagement mechanism may be one or more projections that extend from an interior surface 52 of a distal end 22. In the illustrated exemplary embodiment, for example, each distal end 22A,B includes a cylindrical pin 54A,B extending from an interior surface thereof. The cylindrical pins 54A,B may be sized to engage swage holes provided in exterior surface of the rod receiving portion of a pedicle screw, for example. Alternatively, the implant engagement mechanism may be one or more ridges provided on one or both interior surfaces 52A,B to facilitate gripping of the implant. As discussed below in connection with the embodiment illustrated in FIG. 16, the implant engagement mechanism may be an arcuate rim that is configured to seat within an arcuate groove provided in exterior surface of the rod receiving portion of a pedicle screw.

Figure 11:
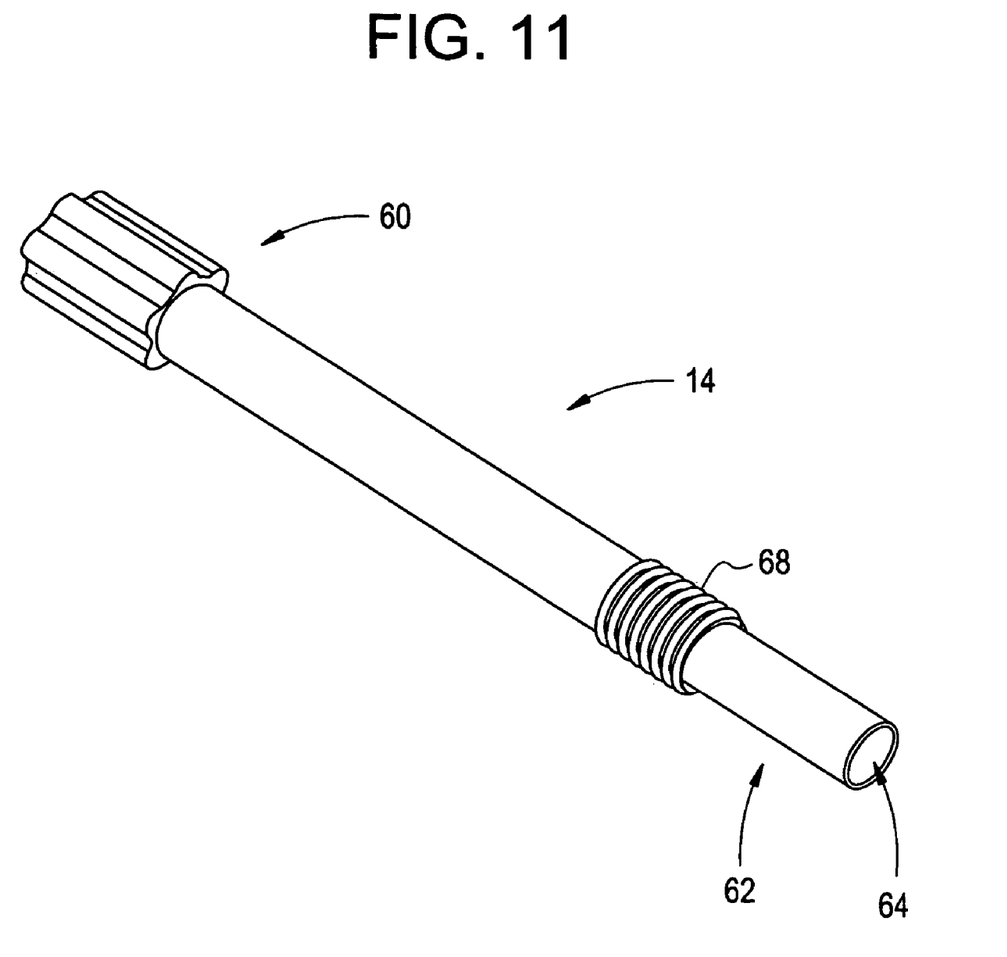
FIG. 11 is a perspective view of the rod adjusting tool of FIG. 1.
Figure 12:
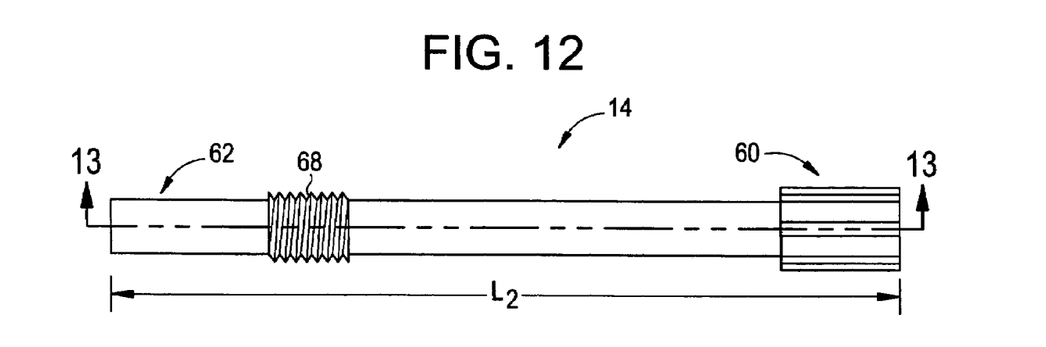
FIG. 12 is a side elevational view of the rod adjusting tool of FIG. 1.
Figure 13:
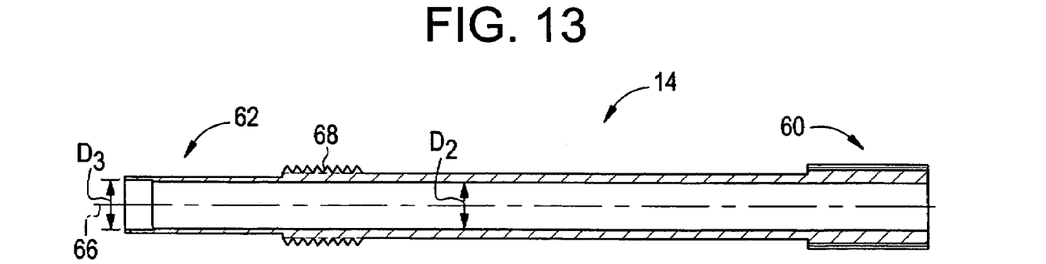
FIG. 13 is a side elevational view in cross section of the rod adjusting tool of FIG. 1, taken along line A-A of FIG. 12.

FIGS. 11-13 illustrate an exemplary embodiment of a rod adjusting tool 14 that is connectable to the bone anchor engaging tool 12 described above and as illustrated in FIGS. 1-3. The rod adjusting tool 14 includes a proximal end 60 and a distal end 62 spaced apart a length $L_2$ from the proximal end 60. The rod adjusting tool 14, in the exemplary embodiment, is generally tubular in shape and has an approximately circular cross-section. One skilled in the art will appreciate that the rod adjusting tool 14 have other cross-sectional configurations, including, for example, elliptical or rectilinear. The rod adjusting tool 14 preferably has a length $L_2$ that is sufficient to span from a skin incision in a patient at the proximal end 60 to proximate a vertebra of the patient at the distal end 62 thereof. The rod adjusting tool 14 may be constructed from any biocompatible material, including a metal such as stainless steel, or a polymer.

The rod adjusting tool 14 includes an inner lumen 64 that extends from the proximal end 60 to the distal end 62 along the longitudinal axis 66. The lumen 64 may be sized and shaped to allow an implant, such as a component of the bone anchor, or another instrument pass therethrough. For example, in the illustrated exemplary embodiment, the lumen 64 has an inner diameter D2 that is greater than or approximately equal to the closure mechanism of the bone anchor engaged by the bone anchor engaging tool 12 and that is greater than or approximately equal to an instrument for securing the closure mechanism to the bone anchor, such as the exemplary driver illustrated in FIG. 14.

The rod adjusting tool 14 preferably has an outer diameter $D_3$ that is less than or approximately equal to the diameter of the collar 40 of the bone anchor engaging tool 12.

As discussed above, the rod adjusting tool 14 may be connectable to and axial adjustable relative to the bone anchor engaging tool 12. In the exemplary embodiment, for example, the rod adjusting tool 14 is adjustable along the longitudinal axis of the bone anchor engaging tool 12 from a first, proximal position, in which the distal end 62 of the rod adjustment tool 14 is displaced from the distal ends 22A,B of the jaw members 18A,B, to a second, distal position in which the distal end 62 of the rod adjustment tool 14 is proximate, relatively, to the distal ends 22A,B of the jaw members 18A,B. During axial advancement from the first position to the second position, the distal end 62 of the rod adjusting tool 14 can engage the spinal rod, or other fixation element, and advance the spinal rod distally relative to the bone anchor. In the exemplary embodiment, the diameter of the rod adjusting tool 14 at the distal end 62 may be greater than outer diameter of the rod receiving portion of the bone anchor such that the distal end 62 may slide over at least a portion of the rod receiving portion of the bone anchor to seat the rod in the bone anchor. The distal end 62 of the rod adjusting tool 14 may be contoured to seat against the spinal rod and facilitate advancement of the rod by the rod adjusting tool 14.

As discussed above, the rod adjusting tool 14 may have external threads 68 that matingly engage internal threads 50A,50B of the jaw members 18A,B to facilitate axial adjustment of the rod adjusting tool 14 and provide mechanical advantage. One skilled in the art will appreciate that other adjustment mechanisms are possible, as discussed above. The proximal end 60 of the rod adjusting tool 14 may include a handle 70 to facilitate rotation of the rod adjusting tool 14 relative to the bone anchor engaging tool 12.

Figure 14:
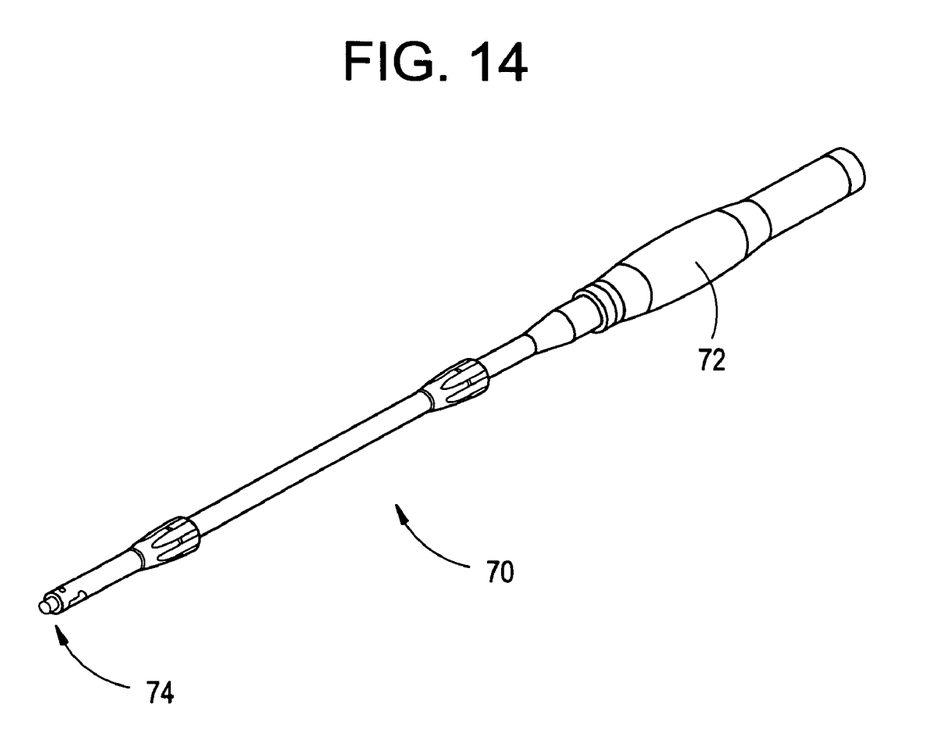
FIG. 14 is a perspective view of an exemplary embodiment of an implant driver.
Figure 15:
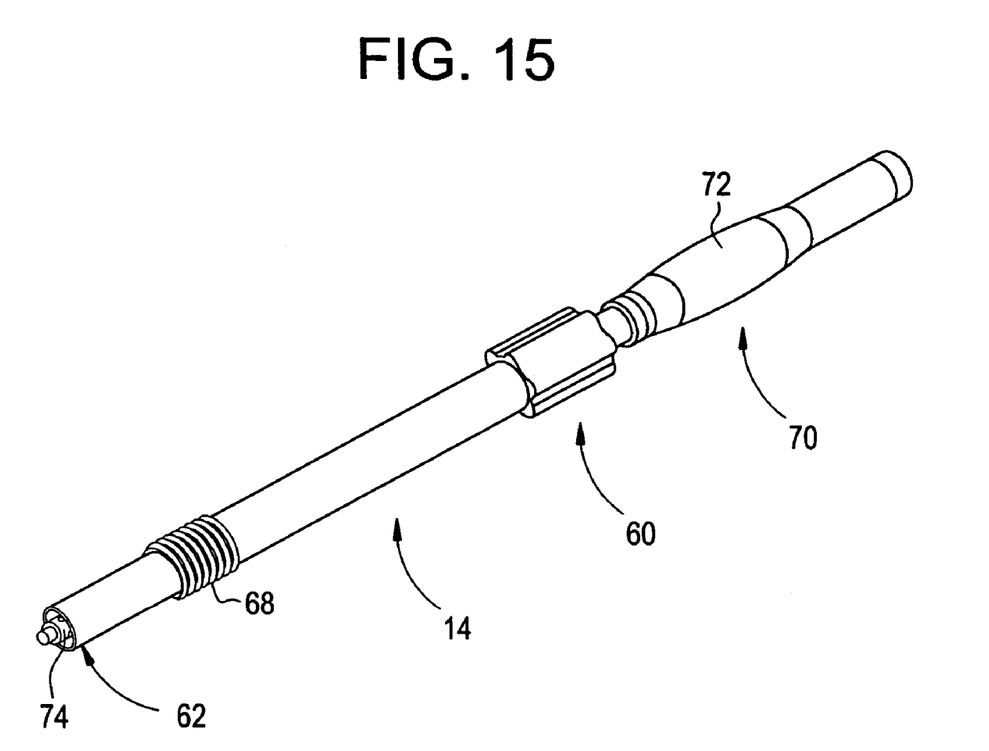
FIG. 15 is a perspective view of the implant driver of FIG. 14 positioned within the rod adjusting tool of FIG. 11.

FIGS. 14 and 15 illustrate an exemplary embodiment of a driver 70 for securing a closure mechanism, or other component of a bone anchor, to the bone anchor. The driver 70 may have a proximal end 72 including a handle and a distal end 74 for engaging the closure mechanism. Any type of closure mechanism can be employed, including internally and/or externally threaded caps, twist-in caps, and multi-component caps. The driver 70 may be axially advanced through the lumen 64 of the rod adjustment tool 14 such that the distal end 74 of the driver 70 is advanced distal to the distal end 62 of the rod adjusting tool 14, as illustrated in FIG. 14. The driver 70 and the rod adjusting tool 14 may include an adjustment mechanism, analogous to one or more of the adjustment mechanisms described above, to facilitate axial adjustment of the driver 70 relative to the rod adjusting tool 14. For example, the driver 70 may include external threads for engagement with internal threads provided within the lumen 64 of the rod adjusting tool 14.

Figure 16B:
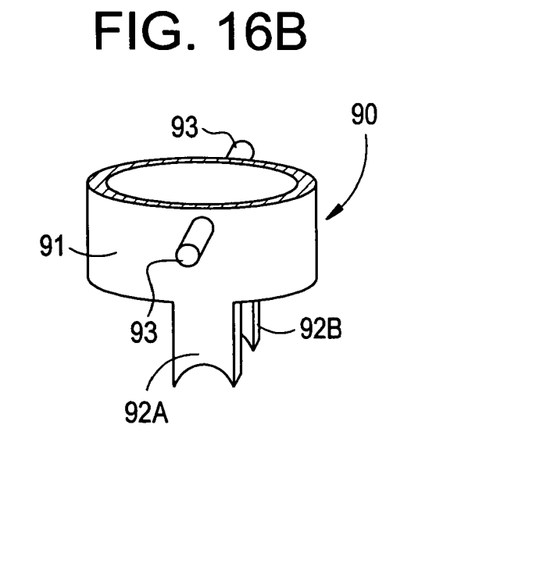
FIG. 16B is perspective view of the exemplary rod engaging member of the instrument of FIG. 16A.

FIGS. 16A and 16B illustrate an alternative exemplary embodiment of the instrument 10, in which a rod engaging member 90 is positioned distal to the distal end 62 of the rod adjustment tool. The rod engaging member 90, in the exemplary embodiment, includes an annular ring 91 and one or more axially oriented extensions 92 that extend distally from the annular ring 91. In the exemplary embodiment, for example, the rod engaging member 90 includes a pair of opposed extensions 92A,B. The extensions 92A,B may be sized to fit within the rod receiving slot 104 of the rod receiving portion 102 of the exemplary bone anchor 100. The distal end of the extensions 94 can engage the spinal rod 110 during axially advancement of the rod engaging member 90 by the rod adjusting tool 14.

The rod engaging member 90 may be rotatably fixed with respect to the rod adjusting tool 14 such that during rotation of the rod adjusting tool 14, the rod engaging member 90 is inhibited from rotating. For example, one or guide pins 93 may be provided on the annular ring 91 that may seat within one or more axially oriented grooves provided on the interior surface of the jaw members 18A,B. In this manner, the rod engaging member 90 may be adjusted axially by the rod adjusting tool 12 with limited, if any rotation of rod engaging member 90. A biasing mechanism may be provided to bias the rod engaging member 90 axially in the proximal direction. For example, one or more axially oriented springs 96 may be provided between the annular ring 91 and the distal ends 22A,B of the jaw members 18A,B.

In the exemplary embodiment illustrated in FIGS. 16A and 16B, the implant engagement mechanism provided on the distal ends 22A,B of the jaw members 18A,B may be an arcuate rim 110A,B that is configured to seat within arcuate grooves 122A,B provided in exterior surface of the rod receiving portion 102 of the bone anchor 100.

Figure 17:
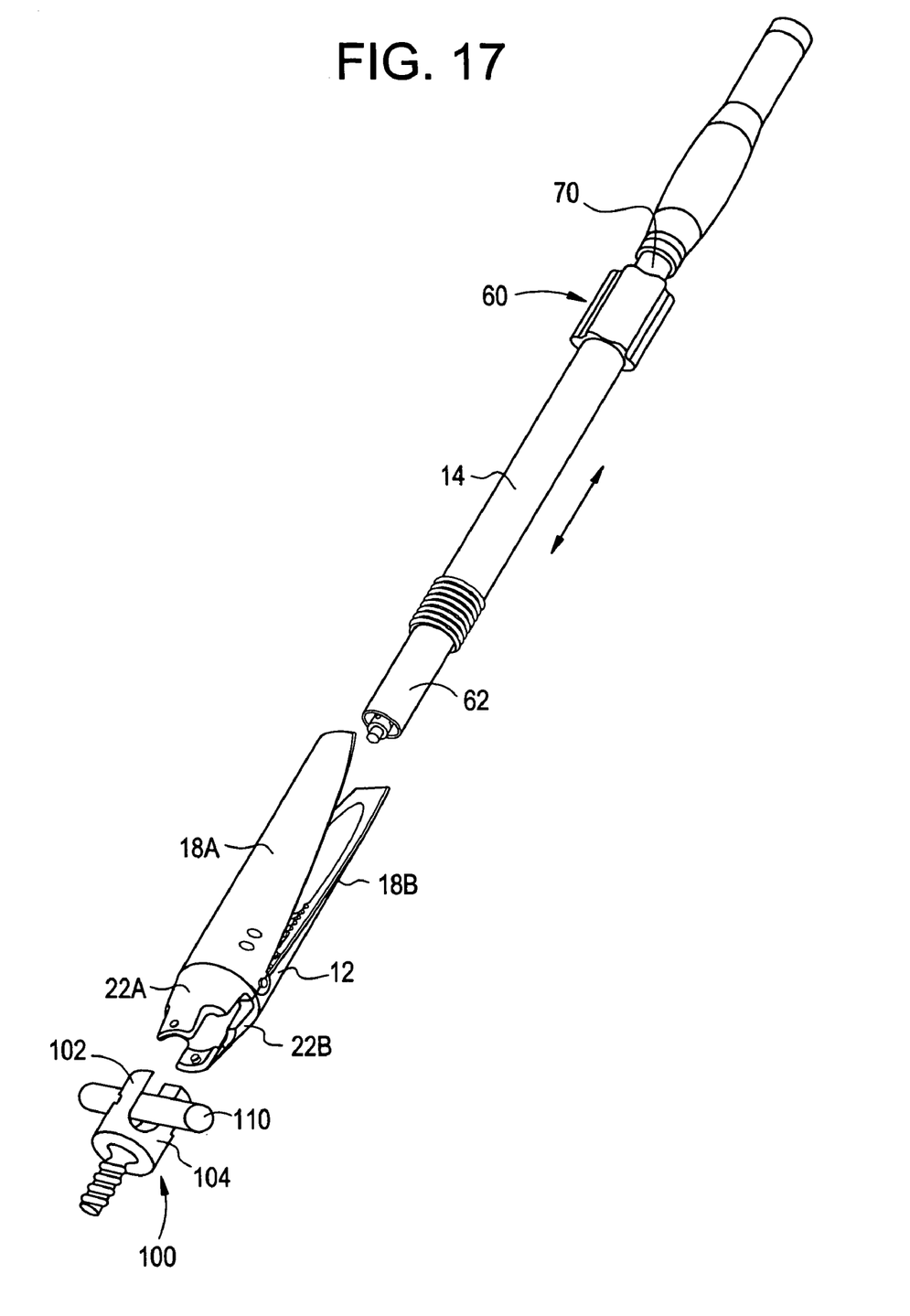
FIG. 17 is a schematic of the instrument of FIG. 1 illustrating engagement of a bone anchor, rod reduction, and delivery of the closure mechanism.

In one exemplary method of operation, the bone anchor engaging tool 12 may be coupled to an exemplary bone anchor 100 by rotating the distal ends 22A,B of the jaw members 18A,B to the open position, advancing the distal ends 22A,B of the jaw members 18A,B about the bone anchor, and rotating the distal ends 22A,B of the jaw members 18A,B to the approximately closed position such that the distal ends 22A,B of the jaw members 18A,B engage the side walls of the rod receiving portion 102 of the bone anchor, as illustrated in FIG. 17. Engagement of the bone anchor engaging tool 12 to the bone anchor 100 can capture the rod 110 between the jaw mwmbers 18 A,B and between the collar 40 and the bone anchor 100. The rod adjusting tool 14 may be advanced axially, by rotating the proximal end 60 of the rod adjusting tool 14, such that the distal end 62 of the rod adjusting tool 14 engages the spinal rod 110 and advances the spinal rod 110 distally in the direction of the bone anchor 100. The rod adjusting tool 14 may be advanced distally to seat the rod 110 in the rod receiving slot 104 of the bone anchor 100. The driver 70 may be employed to position a closure mechanism, such as an externally threaded cap 106, within the rod receiving slot 104 to thereby capture the rod 110 in the rod receiving slot.

In one exemplary embodiment, the driver 70 and closure mechanism may be positioned within the rod adjusting tool 14 during reduction of the spinal rod 110. For example, the driver 70 first may be positioned within the lumen 64 of the rod adjusting tool 14. The distal end 74 of the driver 70 may be advanced to the second position to engage the closure mechanism. The distal end 74 of the driver 70 and the closure mechanism may be adjusted to the first position, in which the closure mechanism is within the lumen 64 of the rod adjusting tool 14. The rod adjusting tool may then be coupled to the bone anchor engaging tool 12 and advanced to reduce the spinal rod, while the distal end 74 of the driver 70 and the closure mechanism are within the lumen 64 of the rod adjusting tool 14. Once the rod 110 is seated, the distal end 72 of the driver 70 may be advanced to secure the closure mechanism to the bone anchor 100.

In other exemplary embodiments, the driver 70 and the closure mechanism may be positioned within the rod adjusting tool 14 after reduction of the spinal rod 110.

The bone anchor engaging tool 12 may be introduced through a minimally invasive incision and/or through an open incision. In minimally invasive applications, the tool 12 may be introduced through a port or canulla or directly through the minimally invasive incision. The tool 12 may be used to create a minimally invasive pathway from the skin incision to the bone anchor for the delivery of implants or secondary instruments.

While the instruments of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. An instrument for engaging an implant comprising:
   a first implant engaging member having a proximal end, a distal end, an arcuate section between the proximal end and the distal end, and an inner surface;
   and a second implant engaging member having a proximal end, a distal end, an arcuate section between the proximal end and the distal end, and an inner surface, the second implant engaging member being pivotally connected to the first implant engaging member about at least one pivot point located proximate the distal ends of the first and second implant engaging members, manipulation of the proximal ends of the first and second implant engaging member causing each of the distal ends to rotate about the at least one pivot point to engage at least a portion of an implant, the arcuate section of the first implant engaging member and the arcuate section of the second implant engaging member connecting to define an annular collar between the first implant engaging member and the second implant engaging member at the pivot point, the annular collar being sized to facilitate the delivery of at least one of an implant or a second instrument therethrough; and an adjustment mechanism to facilitate the connection and adjustment of a second instrument relative to the instrument, the adjustment mechanism comprising a thread formed on the inner surface of the first implant engagement member and a thread formed on the inner surface of the second implant engagement member.

2. The instrument of claim 1, wherein the distal ends of the first implant engaging member and the second implant engaging member are rotatable between an approximately closed position in which the distal ends are proximate one another and an open position in which the distal ends are displaced from one another.

3. The instrument of claim 2, further comprising a biasing mechanism coupled to the first implant engaging member and the second implant engaging member to bias the distal ends to the closed position.

4. The instrument of claim 3, wherein the biasing mechanism comprises at least one spring positioned between the first implant engaging member and the second implant engaging member.

5. The instrument of claim 2, wherein the distal ends when in the closed position are separated a distance that is approximately equal to or less than a width or a diameter of the portion of the implant.

6. The instrument of claim 1, wherein at least one of the distal end of the first implant engagement member and the distal end of the second implant engagement member includes an implant engagement mechanism.

7. The instrument of claim 6, wherein the implant engagement mechanism comprises a projection extending from an interior surface of the distal end at least one of the first implant engaging member and the second implant engaging member.

8. The instrument of claim 7, wherein the projection is a cylindrically shaped pin.

9. The instrument of claim 7, wherein the projection is an arcuate rim.

10. The instrument of claim 6, wherein the implant engagement mechanism comprises a plurality of ridges provided on an interior surface of the distal end at least one of the first implant engaging member and the second implant engaging member.

11. An instrument for engaging a bone anchor comprising,
a first implant engaging member having a proximal end, a distal end having an implant engagement mechanism, an arcuate section between the proximal end and the distal end, and an inner surface;

a second implant engaging member having a proximal end, a distal end having an implant engagement mechanism, an arcuate section between the proximal end and the distal end, and an inner surface, the second implant engaging member being pivotally connected to the first implant engaging member about a pair of pivot points aligned along a pivot axis located proximate the distal ends of the first and second implant engaging members such that manipulation of the proximal ends of the first and second implant engaging member causes each of the distal ends to rotate about the pivot axis between an approximately closed position in which the distal ends are proximate one another and an open position in which the distal ends are displaced from one another, the arcuate section of the first implant engaging member and the arcuate section of the second implant engaging member connecting to define an annular collar therebetween proximate the pivot axis, the annular collar being sized and shaped to facilitate the delivery of a second instrument through the collar; and an adjustment mechanism to facilitate the adjustment of at least a portion of the second instrument through the opening, the adjustment mechanism comprising a thread formed on the inner surface of the first implant engagement member and a thread formed on the inner surface of the second implant engagement member.

12. The instrument of claim 11, further comprising a biasing mechanism coupled to the first implant engaging member and the second implant engaging member to bias distal ends to the closed position.

13. The instrument of claim 12, wherein the biasing mechanism comprises at least one spring positioned between the first implant engaging member and the second implant engaging member.

14. The instrument of claim 11, wherein the distal ends when in the closed position are separated by a distance that is approximately equal to or less than a diameter of the portion of the bone anchor.

15. The instrument of claim 11, wherein the implant engagement mechanisms of the first implant engaging member and the second implant engaging member each comprise a projection extending from an interior surface of the distal ends of the first implant engaging member and the second implant engaging member, respectively.

16. The instrument of claim 15, wherein the projection is a cylindrically shaped pin.

17. The instrument of claim 16, wherein the projection is an arcuate rim.

18. The instrument of claim 11, wherein the implant engagement mechanisms of the first implant engaging member and the second implant engaging member each comprise a plurality of ridges provided on an interior surface of the distal ends of the first implant engaging member and the second implant engaging member.

\* \* \* \* \*